United States Patent [19]

Cordier

[11] 4,073,813
[45] Feb. 14, 1978

[54] PROCESS FOR THE PREPARATION OF UNSATURATED ALCOHOLS

[75] Inventor: Georges Cordier, Francheville, France

[73] Assignee: Rhone-Poulenc Industries, Paris, France

[21] Appl. No.: 733,470

[22] Filed: Oct. 18, 1976

[30] Foreign Application Priority Data

Nov. 3, 1975  France ............................ 75 34364

[51] Int. Cl.² .................................. C07C 29/14
[52] U.S. Cl. .................... 260/617 C; 260/293.51; 260/293.65; 260/293.66; 260/293.67; 260/293.68; 260/263.69; 260/293.9; 260/326.8; 260/345.1; 260/345.2; 260/345.3; 260/345.9 R; 260/347.8; 260/611 R; 260/611 A; 260/614 R; 260/615 R; 260/617 M; 260/618 H; 260/631 H; 260/631.5; 260/638 B
[58] Field of Search ........... 260/638 B, 617 C, 618 H, 260/631 H, 611 A, 614 R, 615 R, 345.1, 345.2, 345.3, 345.9, 346.1, 346.2, 347.8, 327, 329, 332.3, 289, 290, 293.51, 295.65, 293.66, 293.67, 243.68, 293.69, 293.9, 297, 326.5, 326.8, 631.5

[56] References Cited

U.S. PATENT DOCUMENTS

| | | | |
|---|---|---|---|
| 2,098,206 | 11/1937 | Hartung et al. | 260/618 A |
| 2,448,047 | 8/1948 | Peppel | 260/618 H |
| 2,763,696 | 9/1956 | Finch et al. | 260/638 B |
| 2,767,221 | 10/1956 | Ballard et al. | 260/638 B |
| 3,284,517 | 11/1966 | Rylander | 260/638 B |
| 3,466,339 | 9/1969 | Duyverman | 260/638 B |
| 3,471,575 | 10/1969 | Kudo et al. | 260/617 C |
| 3,520,934 | 7/1970 | Dunkel et al. | 260/618 H |
| 3,655,777 | 4/1972 | Rylander et al. | 260/618 H |
| 3,715,404 | 2/1973 | Lundlar et al. | 260/617 C |
| 3,736,265 | 5/1973 | Liggett | 260/638 B |

OTHER PUBLICATIONS

Tuley et al., "J.A.C.S." vol. 47, pp. 3061–3068 (1925).
Adams et al., I, "J.A.C.S.", vol. 48, 477 (1926).
Adams et al., II, "J.A.C.S." vol. 49, 2101 (1927).

*Primary Examiner*—Norman Morgenstern

[57] ABSTRACT

A process for reducing $\alpha,\beta$-ethylenic aldehydes to the corresponding $\alpha,\beta$-ethylenic primary alcohols by hydrogen in the presence of a platinum-containing catalyst which has been pre-reduced in hydrogen at a temperature of at least about 50° C. The process is highly selective in reducing the carbonyl group of the aldehyde in preference to the ethylenic unsaturation and said pre-reduced catalyst can be re-used in a series of aldehyde reductions without substantial loss in activity.

31 Claims, No Drawings

PROCESS FOR THE PREPARATION OF UNSATURATED ALCOHOLS

BACKGROUND OF THE INVENTION

The present invention relates to a process for the preparation of unsaturated alcohols. More particularly, this invention relates to the preparation of α,β-ethylenically unsaturated primary alcohols by catalytic hydrogenation of the corresponding α,β-ethylenic aldehydes.

Among all the processes for obtaining α,β-ethylenic alcohols described in the literature, there are to be found several processes for the catalytic hydrogenation of the corresponding α,β-ethylenic aldehydes. The critical point of the hydrogenation resides in the selectivity of the catalyst, because the ethylenic double bond which is in the conjugated position relative to the carbonyl group can also become hydrogenated under the conditions of reduction of the carbonyl group. The selective hydrogenation of an α,β-ethylenic aldehyde to the corresponding α,β-ethylenic alcohol is rendered more difficult still when one or more ethylenic double bonds are present in a conjugated or non-conjugated position, along side the unsaturation in the α,β-position relative to the formyl or carbonyl group to be reduced.

Various metal catalysts have been proposed for carrying out this hydrogenation; platinum, in its various forms, has for a long time been considered a particularly suitable catalyst. This catalyst can be, in particular, platinum black or mixtures of platinum black and $PtO_2$ obtained by pre-reduction of platinum dioxide at ambient temperature under a low pressure of hydrogen [compare W. F. Tuley and R. Adams, *J. Amer. Chem. Soc.*, 47, pp. 3061 to 3068 (1925)] or metallic platinum deposited on a support, such as charcoal or calcium carbonate (compare U.S. Pat. No. 3,284,517).

However, it is noted that use of these platinum-based catalysts requires the conjoint use of promoters if the formyl or carbonyl group of the α,β-ethylenic aldehyde is to be reduced selectively. Thus, Tuley and Adams employ ferrous chloride or ferrous sulphate (about 0.2 gram atom of Fe per gram atom of platinum), which may or may not be mixed with zinc acetate (about 0.03 gram atom of Zn per gram atom of platinum), while in the above-mentioned U.S. patent, the use of ferrous chloride mixed with silver nitrate (about 0.4 gram atom of Fe and 0.06 gram atom of Ag per gram atom of platinum) is proposed. The reaction wherein the aldehyde substrate is hydrogenated is carried out under hydrogen pressure, at a temperature ranging from 25° C. to 100° C., in general working in a hydroxylic solvent such as a lower saturated aliphatic alcohol, which contains about 0.5 to 2 g. of metallic platinum per mol of aldehyde to be reduced.

The performance achieved by means of the above-mentioned processes is satisfactory; for example, starting from cinnamaldehyde, cinnamyl alcohol is formed predominantly, the remainder (of the product) consisting of 3-phenyl-propan-1-al and/or 3-phenyl-propan-1-ol, and the selectivity of the hydrogenation, measured by the yield of cinnamyl alcohol relative to aldehyde consumed, is greater than 85%; it can reach 90% and even exceed this value.

However, employing noble metals such as platinum is only desirable from an economic point of view if it is possible to recycle the catalyst to the reaction zone without excessively altering the performance obtained with the fresh catalyst. The processes proposed do not offer satisfactory solutions in this respect. In fact, in studying the possibility of recycling the above-mentioned catalyst systems it has been found that, starting from cinnamaldehyde, there is a sharp drop in the catalytic activity at the first attempt at recycling, which manifests itself particularly in a significant lengthening of the reaction time required to achieve a degree of conversion of the aldehyde equivalent to that obtained when the catalyst is first employed, or in a lowering of the degree of conversion if one chooses the same duration for the hydrogenation. This loss in efficiency of the catalyst being recycled thus brings about a reduction in the productivity of the production apparatus and, consequently, reduces the industrial value of such hydrogenation processes.

It was thus desirable to provide a process of hydrogenation in the presence of a platinum-based catalyst which makes it possible to overcome the disadvantages of the prior processes with regard to recycling of the catalyst, while preserving the above-mentioned advantages, especially excellent selectivities in respect of the product of hydrogenation of the formyl group.

There has now been found, and it is this which forms the subject of the present invention, a process which satisfactorily meets this objective.

It is, therefore, an object of the present invention to provide a process for reducing α,β-ethylenic aldehydes to the corresponding α,β-ethylenic primary alcohols, which process overcomes the disadvantages of the prior art.

It is also an object of the present invention to provide a catalytic reduction process whereby the catalyst can be re-used or recycled in the process without a substantial diminution in performance of selectivity in reducing the carbonyl or formyl group without concomitant reduction of the ethylenic unsaturation.

It is a further object to provide a catalytic reduction process which does not require a promoter for the platinum catalyst.

Other objects will be apparent to those skilled in the art from the present description.

GENERAL DESCRIPTION OF THE INVENTION

The present invention relates to a process for reducing α,β-ethylenic aldehydes to the corresponding α,β-ethylenic primary alcohols, which process is conducted in the presence of hydrogen and a platinum-based catalyst in the form of metallic platinum or a platinum-based compound, in which the platinum content has been reduced prior to use in the process in the presence of hydrogen at a temperature of at least about 50° C.

More specifically, the present invention relates to a process for obtaining α,β-ethylenic alcohols of the general formula:

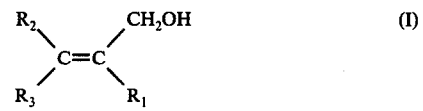

in which $R_1$, $R_2$ and $R_3$, which can be identical or different, represent hydrogen atoms or organic radicals defined below, by hydrogenation of α,β-ethylenic aldehydes of the general formula:

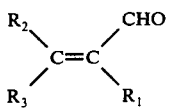

(II)

the process being carried out in a liquid solvent medium in the presence of a platinum-based catalyst, characterized in that the catalyst used is prepared by prior reduction of platinum, taken in the metallic form or in the form of a platinum-based compound, by means of hydrogen at a temperature of at least about 50° C.

In the text which follows, the term "lower alkyl radicals" will be applied to linear or branched alkyl radicals containing from 1 to 4 carbon atoms such as the methyl, ethyl, n-propyl, isopropyl, n-butyl, iso-butyl and t-butyl radicals. The term "lower alkoxy radicals" will be applied to linear or branched alkoxy radicals containing from 1 to 4 carbon atoms such as the methoxy, ethoxy, propoxy, isopropoxy and butoxy radicals. The term "lower alkenyl radicals" will be applied to radicals containing from 2 to 4 carbon atoms such as the vinyl, prop-1-enyl, allyl, isopropenyl, but-3-enyl, but-2-enyl, but-1-enyl and 1-methyl-prop-2-enyl radicals.

More specifically, the various radicals shown in the formulae (I) and (II) have the following meaning:

$R_1$ symbolizes:

(a) a linear or branched alkyl radical having from 1 to 8 carbon atoms;

(b) a lower alkoxy radical;

(c) a cycloalkyl or cycloalkenyl radical containing from 5 to 6 carbon atoms and, where relevant, 1 or 2 ethylenic double bonds, the radical optionally being substituted by 1 to 3 lower alkyl or alkoxy radicals;

(d) an aryl radical containing 1 or 2 fused benzene nuclei, and optionally substituted by 1 to 3 lower alkyl or alkoxy radicals; or, (e) an aralkyl radical containing from 1 to 2 carbon atoms in the alkyl radical and 1 or 2 fused benzene nuclei in the aryl radical.

$R_2$ and $R_3$, which may be identical or different, represent:

(a) linear or branched alkyl radicals containing from 1 to 30 carbon atoms and optionally substituted by lower alkoxy radicals, by cycloalkyl or cycloalkenyl radicals containing from 5 to 8 carbon atoms (which radicals can carry 1 to 3 lower alkyl, alkoxy or alkenyl radicals), or by heterocyclic radicals with 5 or 6 chain members and containing a hetero-atom such as sulphur, oxygen or nitrogen (these radicals optionally possessing 1 or 2 ethylenic double bonds);

(b) lower alkoxy radicals;

(c) linear or branched alkenyl radicals containing from 2 to 30 carbon atoms and from 1 to 12 conjugated or non-conjugated ethylenic double bonds, these radicals optionally being substituted by lower alkoxy radicals or by cycloalkyl, cycloalkenyl or heterocyclic radicals, such as those defined under (a);

(d) cycloalkyl or cycloalkenyl radicals containing from 5 to 8 carbon atoms and, where relevant, 1 or 2 ethylenic double bonds, these radicals optionally being substituted by 1 to 3 lower alkyl, alkoxy or alkenyl radicals;

(e) aryl radicals containing 1 or 2 fused or non-fused benzene nuclei, these radicals optionally being substituted by 1 to 3 lower alkyl, alkoxy or alkenyl radicals;

(f) aralkyl radicals containing from 1 to 5 carbon atoms in the alkyl radical and 1 or 2 fused or non-fused benzene nuclei (the benzene nucleus or nuclei optionally being substituted by 1 to 3 lower alkyl, alkoxy or alkenyl radicals); or, (g) heterocyclic radicals with 5 or 6 chain members, containing a hetero-atom such as sulphur, oxygen or nitrogen and optionally carrying 1 or 2 ethylenic double bonds, the radicals being substituted, where appropriate, by 1 or 2 lower alkyl or alkoxy radicals.

$R_2$ or $R_3$ can form, with $R_1$ and the carbon atoms to which these various radicals are bonded, an aliphatic hydrocarbon ring containing from 5 to 7 carbon atoms and 1 or 2 ethylenic double bonds (these radicals optionally being substituted by 1 to 3 lower alkyl or alkoxy radicals), in which case two of the above-mentioned radicals $R_2$ or $R_3$ and $R_1$ together form a divalent alkylene or alkenylene radical containing from 3 to 5 carbon atoms, this radical optionally being substituted by 1 to 3 lower alkyl radicals.

$R_2$ or $R_3$ can furthermore form, with $R_1$ and the carbon atoms to which they are bonded, a heterocyclic ring with 5 or 6 chain members (containing 1 or 2 ethylenic double bonds), via a hetero-atom chosen from the group consisting of oxygen, sulphur and nitrogen (in which case the radicals $R_2$ or $R_3$ form, with the radical $R_1$, a divalent radical containing a terminal or non-terminal hetero-atom and, where appropriate, containing an ethylenic double bond).

$R_2$ and $R_3$ can together, and with the carbon atom to which they are bonded, form an aliphatic hydrocarbon ring such as that defined above for $R_1$ and $R_2$ or $R_3$, in which case $R_2$ and $R_3$ together form a divalent alkylene or alkenylene radical containing from 4 to 6 carbon atoms, which is optionally substituted by 1 to 3 alkyl radicals.

By way of specific examples of radicals $R_1$ there may be mentioned:

alkyl radicals such as the methyl, ethyl, n-propyl, iso-propyl, n-butyl, iso-butyl, t-butyl, n-pentyl, iso-pentyl, tertiary amyl and n-hexyl radicals;

alkoxy radicals such as the methoxy, ethoxy, propoxy, isopropoxy and butoxy radicals;

cycloalkyl or cycloalkenyl radicals such as the cyclopentyl, cyclohexyl and cyclohexenyl radicals;

aryl radicals such as the phenyl, tolyl, xylyl and α-naphthyl radicals; and, aralkyl radicals such as the benzyl and phenethyl radicals.

The following may be mentioned particularly as illustrative examples of radicals $R_2$ and $R_3$:

alkyl radicals such as the methyl, ethyl, propyl, isopropyl, n-butyl, iso-butyl, n-pentyl, n-hexyl, 3-methylhexyl, n-heptyl, n-octyl, 4-methyl-octyl, n-nonyl, 4,8-dimethylnonyl, n-decyl, n-undecyl, n-dodecyl, methoxymethyl, 2-methoxyethyl, [3'-methyl-cyclohex-3'-enyl]-methyl, [2', 6', 6'-trimethyl-cyclohex-1'-enyl]-methyl, 2-[2', 6', 6'-trimethyl-cyclohex-1'-enyl]-ethyl, 6-[2', 6', 6'-trimethyl-cyclohex-1'-enyl]-4-methyl-hexyl and 2-[furyl-2']-ethyl radicals;

alkoxy radicals such as the methoxy, ethoxy, propoxy, isopropoxy and butoxy radicals;

alkenyl radicals such as the vinyl, prop-1-enyl, allyl, isoprenyl, 1-methyl-prop-2-enyl, but-1-enyl, but-2-enyl, but-3-enyl, pent-3-enyl, 4-methyl-pent-3-enyl, 3,4-dimethylpent-3-enyl, 2,4-dimethyl-pent-3-enyl, 1,4-dimethyl-pent-3-enyl, hex-2-enyl, hex-3-enyl, buta-1,3-dienyl, 2-methyl-buta-1,3-dienyl, 3-methyl-buta-1,3-dienyl, 3-methyl-penta-1,3-dienyl, 2,4-dimethyl-penta-2,4- dienyl, hexa-3,5-dienyl, 4,8-dimethyl-nona-3,7-dienyl, 4,8-dimethyl-nona-3,8-dienyl, 4,8, 12-trimethyl-trideca-3,7,11-trienyl, 2-[2',6',6'-trimethylcyclohex-1'-enyl]-vinyl, 3-[2', 6', 6'-trimethyl-cyclohex-1'-enyl]-1-methyl-prop-1-enyl, 5-[2', 6', 6'-trimethyl-cyclohex-1'-enyl]-3-methyl-penta-1,3-dienyl, 5-[2', 6', 6'-trimethylcyclohex-1',3'-dienyl]-3-methyl-penta-1,3-dienyl, 6-[2', 6', 6'-trimethyl-cyclohex-1'-enyl]-4-methyl-hexa-1,3,5-trienyl and 6-[furyl-2']-3-methyl-hex-3-enyl radicals;

cycloalkyl radicals such as cyclohexyl, 2-methylcyclohexyl, 2,6,6,-trimethyl-cyclohexyl and cycloheptyl;

cyloalkenyl radicals such as cyclohex-1-enyl, 2,6,6-trimethyl-cyclohex-1-enyl and 2,6,6-trimethyl-cyclohexa-1,3-dienyl;

aryl radicals such as the phenyl, tolyl, xylyl or α- or β-naphthyl radicals;

aralkyl radicals such as the benzyl, p-methyl-benzyl, phenethyl and 3-phenyl-propyl radicals; and, heterocyclic radicals such as furyl-2, furyl-3 and pyranyl-3.

Among the divalent radicals formed conjointly by $R_2$ or $R_3$ with $R_1$ there may especially be mentioned the trimethylene, tetramethylene and 2-methyl-propylene radicals, and the radicals of the formula:

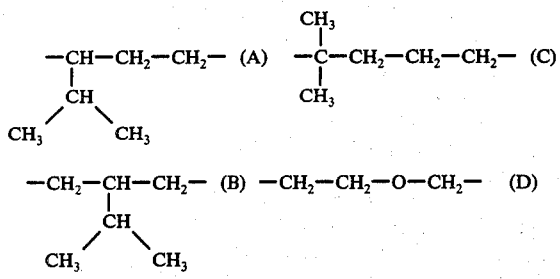

As examples of divalent radicals formed by $R_2$ and $R_3$ together, there may be mentioned the tetramethylene, pentamethylene and hexamethylene radicals.

In the formulae (I) and (II), the symbols $R_1$, $R_2$ and $R_3$ preferably represent the following:

$R_1$ and $R_2$, which may be identical or different, represent hydrogen, a linear or branched alkyl radical having from 1 to 8 carbon atoms, or a lower alkoxy radical; and $R_3$ represents a linear or branched alkyl radical containing from 1 to 10 carbon atoms and optionally substituted by methoxy and ethoxy radicals or by cyclohexyl or cyclohexenyl radicals carrying from 1 to 3 methyl groups, or by a furyl radical; a linear or branched alkenyl radical containing from 2 to 30 carbon atoms and from 1 to 12 conjugated or non-conjugated ethylenic double bonds, and optionally substituted by methoxy or ethoxy radicals or by cyclohexyl, cyclohexenyl, cyclohexadienyl or furyl radicals containing from 1 to 3 methyl substituents; a cycloalkyl or cycloalkenyl radical containing from 5 to 6 carbon atoms and, where relevant, 1 or 2 ethylenic double bonds, and optionally substituted by 1 to 3 methyl or methoxy radicals; an aryl radical containing 1 or 2 fused benzene nuclei and optionally substituted by 1 to 3 methyl or methoxy radicals; an aralkyl radical containing from 1 to 2 carbon atoms in the alkyl radical and 1 or 2 fused benzene nuclei, the benzene nucleus or nuclei being optionally substituted by 1 to 3 methyl or methoxy radicals; and an oxygen-containing heterocyclic radical with 5 or 6 chain members, which optionally contains 1 or 2 ethylenic double bonds and, where appropriate, is substituted by 1 or 2 methyl or methoxy radicals; alternatively, $R_3$ forms, with $R_1$, a tetramethylene radical or one of the radicals (C) or (D), and, with $R_2$, the tetramethylene and pentamethylene radical.

More preferably still:

$R_1$ represents a hydrogen atom or a methyl, ethyl, propyl, isopropyl, n-butyl, n-pentyl, n-hexyl, methoxy, ethoxy, propoxy or butoxy radical;

$R_2$ represents a hydrogen atom or a methyl, ethyl, methoxy or ethoxy radical;

$R_3$ represents one of the following radicals:

methyl, ethyl, n-propyl, n-butyl, n-pentyl, n-hexyl, n-heptyl, methoxymethyl, 2-methoxy-ethyl, [3'-methyl-cyclohex-3'-enyl]-methyl, [2', 6', 6'-trimethyl-cyclohex-1'-enyl]-methyl, 2-[2', 6', 6'-trimethyl-cyclohex-1'-enyl]-ethyl or 2-[furyl-2']-ethyl;

vinyl, prop-1-enyl, but-1-enyl, but-2-enyl, but-3-enyl, pent-3-enyl, 4-methyl-pent-3-enyl, 1,4-dimethyl-pent-3-enyl, 4,8-dimethyl-nona-3,7-dienyl, 4,8,12-trimethyl-trideca-3,7,11-trienyl, 3-[2', 6', 6'-trimethyl-cylohex-1'-enyl]-1-methyl-prop-1-enyl, 5-[2', 6', 6'-trimethyl-cyclohex-1'-enyl]-3-methyl-penta-1,3-dienyl, 6-[2', 6', 6'-trimethyl-cyclohex-1'-enyl]-4-methyl-hexa-1,3,5-trienyl and 6-[furyl-2']3-methylhex-3-enyl;

cyclohexyl and cyclohex-1-enyl;

phenyl, tolyl, benzyl and phenethyl; and furyl-2 and furyl-3;

alternatively, $R_3$ forms, with $R_1$, a tetramethylene radical or the radical (C).

The following may be mentioned, without implying a limitation, as examples of α, β-ethylenic aldehydes of the formula (II) which may be employed as starting materials: but-2-enal (or crotonaldehyde), 2-methyl-but-2-enal (or tiglicaldehyde), 3-methyl-but-2-enal, 2-methoxy-but-2-enal, 3-methoxybut-2-enal, 4-methoxy-but-2-enal, pent-2-enal, 2-methyl-pent-2-enal, 3-methyl-pent-2-enal, hex-2-enal, 2-ethyl-hex-2-enal, 2-n-butyl-oct-2-enal, 2-n-hexyl-dec-2-enal, 4-[3'-methylcyclohex-3'-enyl]-but-2-enal, 4-[2', 6', 6'-trimethyl-cyclohex-1'-enyl]-2-methyl-but-2-enal, 5-[2', 6', 6'-trimethyl-cyclohex-1'-enyl]-3-methyl-pent-2-enal, 5-[furyl-2']-2-methyl-pent-2-enal, penta-2,4-dienal, hexa-2,4-dienal, hepta-2,4-dienal, hepta-2,6-dienal, 3-methyl-hepta-2,6-dienal, octa-2,6-dienal, 2-methyl-octa-2,6-dienal, 3,7-dimethyl-octa-2,6-dienal (or citral), 3,7,11-trimethyl-dodeca-2,6,10-trienal (or farnesal), 7,11-dimethyl-dodeca-2,6,10-trienal, 3,7,11-15-tetramethylhexadeca-2,6,10,14-tetraenal, 6-[2', 6', 6'-trimethyl-cyclohex-1'-enyl]-4-methyl-hexa-2,4-dienal, 8-[2', 6', 6'-trimethylcyclohex-1'-enyl]-2,6-dimethyl-octa-2,4,6-trienal, 9-[2', 6', 6'-trimethyl-cyclohex-1'-enyl]-3,7-dimethyl-nona-2,4,6,8-tetraenal (or retinal), 9-[furyl-2']-2,6-dimethyl-nona-2,6-dienal, 3-cyclohexyl-prop-2-enal, 3-[cyclohex-1'-enyl]-prop-2-enal, 3-phenyl-prop-2-enal (or cinnamaldehyde), 2-n-pentyl-3-phenyl-prop-2-enal, 2-n-hexyl-3-phenyl-prop-2-enal, 3-methyl-3-phenyl-prop-2-enal, 4-phenyl-but-2-enal, 3-methyl-4-phenylbut-2-enal, 5-phenyl-pent-2-enal, 3-methyl-3-p-tolyl-prop-2-enal, 3-[furyl-2']-prop-2-enal, 3-[furyl-3']-prop-2-enal, 1-formyl-2,6,6,-trimethyl-cyclohex-1-ene (or β-cyclocitral) and 1-formyl-cyclohexene.

The process of selective hydrogenation according to the present invention is particularly applicable to the following aldehyde compounds: 2-methyl-but-2-enal, 3-methyl-but-2-enal, hexa-2,4-dienal, octa-2,6-dienal, 3,7-dimethyl-octa-2,6-dienal, 3,7,11-trimethyl-dodeca-2,6,10-trienal, 9-[2', 6', 6'-trimethylcyclohex-1'-enyl]-3,7-dimethyl-nona-2,4,6,8-tetraenal, 3-phenylprop-2- suspension of pre-reduced platinum plays the role of both a catalyst and a medium for the hydrogenation of the aldehyde substrate. The composition of the mixtures of water with the above-mentioned alcohols, their ethers or their esters, which can thus be used, is also not critical; for example, mixtures containing from about 5 to 60% by weight of water and from about 95 to 40% by weight of organic solvent are used.

As regards the subsequent hydrogenation of the $\alpha,\beta$-ethylenic aldehyde, it can be carried out in a simple manner, for example, by introducing the aldehyde compound, the chosen solvent and the catalyst based on pre-reduced platinum into a hydrogenation apparatus in the absence of air, or preferably, by adding the aldehyde compound to the crude suspension resulting from the pre-reduction of the platinum, in the chosen solvent, in the above-mentioned apparatus. The reactor is then flushed with hydrogen and is pressurized with this gas, after which the medium is heated to the appropriate temperature and the mixture is stirred until an amount of hydrogen corresponding to the fixing of one molecule of hydrogen per molecule of aldehyde has been consumed.

The amount of platinum, used in the metallic form or in the form of a platinum-based compound, which is employed can vary—expressed as weight of metallic platinum per 100 g. of aldehyde substrate to be reduced-between about 0.01 and 4 g., and preferably between about 0.05 and 2 g.

The concentration by weight of $\alpha,\beta$-ethylenic aldehyde in the hydrogenation medium is not critical and can vary within wide limits. It is usually between about 2 and 60% and preferably between about 10 and 50%.

The value of the hydrogen pressure required can be equal to atmospheric pressure, though higher pressures are preferred; pressures of between about 1 and 200 bars and preferably between about 5 and 100 bars are in general suitable.

The temperature at which the hydrogenation of the aldehyde is carried out can vary within wide limits. More particularly, the hydrogenation is carried out at moderately elevated temperatures which can vary from about 20° C. to 150° C., and preferably from about 50° C. to 120° C.

When the hydrogenation of the aldehyde substrate is carried out in water or in solvent mixtures containing water, it is found that it can be advantageous to bring the pH of the mixture of a value of between 6 and 10 and preferably between 7 and 9. The appropriate pH can be obtained by carrying out the reaction in the presence of a defined amount of an appropriate basic agent such as, for example, an alkali metal hydroxide, alkali metal carbonate or alkali metal acetate. NaOH, KOH, $Na_2CO_3$, $K_2CO_3$ or $CH_3COOLi$ may be mentioned in this respect. The reaction can also be carried out in the presence of a buffer mixture containing salts of inorganic oxyacids, the nature and amounts of which in the mixture are such that the ph of their solutions lies between the above-mentioned values. In this respect, the following systems are suitable: phosphoric acid/monobasic phosphate/dibasic phosphate of an alkali metal; boric acid/borate of an alkali metal; carbonate/bicarbonate of an alkali metal. Particularly indicated buffer systems consist of equimolar mixtures of the monobasic phosphate and dibasic phosphate of sodium or of potassium, or equimolar mixtures of the carbonate and the bicarbonate of sodium or of potassium.

Once the desired amount of hydrogen has been absorbed, the autoclave is cooled, if necessary, and then depressured, and the catalyst is separated from the reaction mixture by filtration under an inert gas atmosphere (nitrogen) or by decantation. The solvent contained in the liquid hydrogenation phase is then removed by simple distillation. The corresponding $\alpha,\beta$-ethylenic primary alcohol is thus isolated, which is generally of sufficient purity to enable it subsequently to be used directly as a synthesis intermediate in other chemical reactions (production of esters or of copolymers). This product can also be subjected to a purification treatment by rectification, for example, if the product is used in perfumery, as many ethylenic alcohols are.

The catalyst which is separated off is stored in the absence of air and can easily be used, in its existing state, to carry out a new aldehyde hydrogenation reduction reaction. The process according to the present invention is particularly suitable for continuous operation.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLES 1 to 8

These examples relate to the hydrogenation of 3-phenyl-prop-2-enal (cinnamaldehyde) to the corresponding ethylenic alcohol (cinnamyl alcohol), using platinum in the form of a mass containing 5% by weight of noble metal deposited on charcoal (specific surface area: about 1000 $m^2/g$.); the amount employed, expressed as weight of metallic platinum per 100 g. of cinnamaldehyde to be reduced, is 0.38 g. These examples are carried out varying the temperature and pressure conditions and the duration of the first stage comprising pre-reduction of the platinum employed by means of hydrogen. The second stage, comprising hydrogenation of the aldehyde, is carried out identically in the majority of these examples.

(a) Pre-reduction of the platinum

10 $cm.^3$ of isopropyl alcohol containing 30% by weight of water, and 0.2 g. of platinum deposited on charcoal (representing 0.01 g. of metallic platinum) are introduced into a 125 $cm.^3$ stainless steel autoclave equipped with a knock-type agitation system and connected to a supply of hydrogen under pressure.

The reactor is flushed with nitrogen and then with hydrogen. The stirring is started and the contents of the autoclave are heated to the desired temperature. The hydrogen pressure is then set up and stirring is continued while maintaining the temperature and the pressure at the chosen values for a period ranging from 2 to 16 hours.

The table which follows summarizes the various working conditions which have been employed in these examples, as regards the pre-reduction of the platinum:

| PRE-REDUCTION | | | |
|---|---|---|---|
| Example | Temperature | Pressure | Duration |
| 1 | 50° C. | 5 bars | 16 hours |
| 2 | 70° C. | 5 bars | 16 hours |
| 3 | 100° C. | 20 bars | 2 hours |
| 4 | 100° C. | 20 bars | 16 hours |
| 5 | 100° C. | 120 bars | 2 hours |
| 6 | 100° C. | 180 bars | 2 hours |
| 7 | 130° C. | 120 bars | 2 hours |

(b) Reduction of the cinnamaldehyde once the pre-reduction stage is finished, the autoclave is cooled to 20° C. and is then degassed, and 2.64 g. (0.02 mol) of cinnamaldehyde and 0.5 cm.$^3$ of an aqueous lithium acetate solution, containing 0.2 mol/liter of $CH_3COOli$, are introduced into the contents of the autoclave.

The reactor is flushed with nitrogen and then with hydrogen. The stirrer is started and the contents of the autoclave are heated to a temperature of 70° C. A pressure of 45 bars is then set up with hydrogen and the stirring is continued while maintaining the temperature and the pressure at the above-mentioned values until the volume of hydrogen absorbed corresponds approximately to the amount theoretically necessary (0.02 mol) for converting the aldehyde to the alcohol.

It should be noted that Example 5 was repeated, carrying out the hydrogenation of the aldehyde at 25° C. under 5 bars of hydrogen (Example 8).

The duration of the reaction of hydrogenation of the cinnamaldehyde is on average between 3 hours, 30 minutes and 4 hours.

After this time, the autoclave is cooled to 20° C. and then degassed, and the reaction mixture is filtered under a nitrogen atmosphere. The reactor and the catalyst on the filter (which is placed under nitrogen) are then washed successively with 10 cm.$^3$ of isopropyl alcohol containing 30% by weight of water.

The filtrate obtained is studied by vapor phase chromatographic analyses. It is thus found that it contains a little unreacted cinnamaldehyde and a mixture consisting of 3-phenyl-prop-2-enol (cinnamyl alcohol), 3-phenyl-propanal and 3-phenyl-propanol. The degree of conversion (DC) of the aldehyde is between 84% and 93%.

The table which follows indicates, for these various examples, the yields of cinnamyl alcohol ( ⌐ OH ), of 3-phenylpropanal ( ⌐ O )

and of 3-phenyl-propanol ( ⌐ OH ), expressed relative to the cinnamaldehyde which has reacted.

| | YIELDS | | |
|---|---|---|---|
| Example | OH | O | OH |
| 1 | 84.8% | 9.4% | 5.8% |
| 2 | 87.9% | 7.3% | 4.8% |
| 3 | 86.6% | 10.6% | 2.8% |
| 4 | 87% | 6.5% | 6.5% |
| 5 | 87.8% | 8.2% | 4% |
| 6 | 87.7% | 8.8% | 3.5% |
| 7 | 87.8% | 9% | 3.2% |
| 8 | 85.2% | 12% | 2.8% |

By way of comparison

An experiment was carried out without pre-reducing the platinum, the cinnamaldehyde being hydrogenated under the conditions of Examples 1 to 7 (Experiment A);

an experiment was carried out pre-reducing the platinum at 25° C. under 5 bars of hydrogen for 16 hours and then hydrogenating the aldehyde substrate under the conditions of Examples 1 to 7 (Experiment B); and another experiment was carried out without prereducing the platinum, and hydrogenating the cinnamaldehyde in accordance with the data of U.S. Pat. No. 3,284,517 (Experiment C); this means that the following are introduced into the 125 cm.$^3$ autoclave: 50 cm.$^3$ of ethyl alcohol, 14.5 g. (0.11 mol) of cinnamaldehyde, 2 g. of platinum deposited, at the rate of 5% by weight, on charcoal, 0.026 g. of $FeCl_2$ (0.0002 gram atom of Fe, equivalent to 0.4 gram atom of Fe/gram atom of Pt), and 0.005 g. of $AgNO_3$ (0.00003 gram atom of Ag, equivalent to 0.06 gram atom of Ag/gram atom of Pt).

The hydrogenation is carried out as indicated in Example 8, at a temperature of 25° C. and under 5 bars of hydrogen.

The table which follows summarizes the results obtained at the end of Experiments A, B and C:

| | | | YIELDS/aldehyde reacted | | |
|---|---|---|---|---|---|
| Experiment | Duration | DC of aldehyde | OH | O | OH |
| A | 12 hours | 77.3% | 61.2% | 27% | 11.8% |
| B | 10 hours, 50 min. | 73.8% | 79.5% | 15.2% | 5.3% |
| C | 5 hours | 92.1% | 87.8% | 5.3% | 6.9% |

EXAMPLE 9

This example relates to the hydrogenation of cinnamaldehyde to the corresponding ethylenic alcohol (cinnamyl alcohol), employing platinum dioxide containing 78% by weight of noble metal.

(a) Pre-reduction of the platinum 10 cm.$^3$ of isopropyl alcohol containing 30% by weight of water and 0.015 g. of $PtO_2$ (equivalent to 0.0117 g. of metallic platinum) are introduced into a 125 cm.$^3$ stainless steel autoclave equipped with a knock-type agitation system and connected to a supply of hydrogen under pressure.

The pre-reduction is carried out in accordance with the procedure described for Examples 1 to 8 at a temperature of 70° C. and under a pressure of 120 bars of hydrogen; its duration is 2 hours.

(b) Reduction of the cinnamaldehyde

At the end of this time, after cooling, the same amounts of cinnamaldehyde and of aqueous lithium acetate solution (containing 0.2 mol/liter) as those used in the course of the examples carried out in the presence of prereduced platinum on charcoal, are introduced into the autoclave. The method of working is as already described for Examples 1 to 7.

After having absorbed the amount theoretically required (0.02 mol) to convert the aldehyde to cinnamyl alcohol, the autoclave is cooled to 20° C. and then let down. The liquid phase from the hydrogenation is withdrawn, leaving the catalyst in the autoclave under a nitrogen atmosphere, and is then analyzed by vapor phase chromatography.

(c) Recycling of the catalyst

A fresh charge of reactants, namely, 10 cm.$^3$ of isopropyl alcohol containing 30% by weight of water, 2.64 g. of cinnamaldehyde and 0.5 cm.$^3$ of the aqueous lithium acetate solution containing 0.2 mol/liter of CH$_3$COOLi, is introduced into the autoclave containing the catalyst which has been used and placed under nitrogen. The reduction of the aldehyde is thereafter carried out in accordance with the working method described for the fresh catalyst. The catalyst was in this way recycled 8 times in succession (without pre-reducing the platinum before re-using it).

The results are shown in the table below:

Pre-reduction of the PtO$_2$ 50 cm.$^3$ of ethyl alcohol and 0.2 g. of PtO$_2$, containing 82.9% by weight of the noble metal (equivalent to 0.166 g. of metallic platinum) are introduced into a 250 cm.$^3$ autoclave.

The reactor is flushed with nitrogen and then with hydrogen. The agitation is started and a hydrogen pressure of 3 bars is then set up. The pre-reduction is carried out while agitating the reactor at ambient temperature for 1 hour, 30 minutes.

Reduction of the cinnamaldehyde

The autoclave is opened and the following are introduced: 13.2 g. (0.1 mol) of cinnamaldehyde, 1.75 cm.$^3$ of an aqueous FeCl$_2$ solution containing 0.11 mol/liter (0.0002 gram atom of Fe, equivalent to 0.24 gram atom of Fe/gram atom of Pt) and 3 cm.$^3$ of an aqueous solution of (CH$_3$COO)$_2$Zn containing 0.01 mol/liter (0.00003 gram atom of Zn, equivalent to 0.035 gram atom of Zn/gram atom of Pt).

The reactor is flushed with nitrogen and then with hydrogen. The stirring is started and a hydrogen pressure of 3 bars is then set up. The experiment is carried out at 20° C. until the theoretical amount of hydrogen (0.1 mol) has been absorbed. The total duration of the reaction is 4 hours, 15 minutes.

At the end of this time, the liquid hydrogenation phase is withdrawn, leaving the catalyst in the auto-

| Example 9 | Duration | | DC of aldehyde | YIELDS/ aldehyde reacted | | |
|---|---|---|---|---|---|---|
| | | | | ⎡OH⎤ | ⎡O⎤ | ⎡OH⎤ |
| Fresh catalyst | 3 hrs. | 25 min. | 95.4% | 93.3% | 2.6% | 4.1% |
| 1st recycling | 1 hr. | 45 min. | 91.7% | 95.9% | 1.8% | 2.3% |
| 2nd recycling | 1 hr. | 20 min. | 95.6% | 96.3% | 1.4% | 2.3% |
| 3rd recycling | | 35 min. | 88.9% | 95.7% | 1.8% | 2.5% |
| 4th recycling | 1 hr. | | 98.8% | 95.9% | 0.6% | 3.5% |
| 5th recycling | | 55 min. | 95.4% | 96.9% | 1.1% | 2% |
| 6th recycling | | 35 min. | 85.7% | 97.4% | 1.3% | 1.3% |
| 7th recycling | | 40 min. | 93.5% | 96.8% | 1% | 2.2% |
| 8th recycling | | 40 min. | 96.5% | 96.6% | 1% | 2.4% |

By way of comparison

An experiment was carried out pre-reducing the platinum oxide at 20° C. under 100 bars of hydrogen for 16 hours and then hydrogenating the aldehyde substrate under the usual conditions (Experiment D); the yield of cinnamyl alcohol relative to the aldehyde converted is, under these conditions, no more than 71%.

Another experiment on the hydrogenation of cinnamaldehyde was carried out in accordance with the data of Tuley and Adams, supra; a pre-reduction of the PtO$_2$ is first carried out at ambient temperature (20° C.) under a low pressure of hydrogen, and the cinnamaldehyde is then reduced, after having introduced the aldehyde and the promoters [FeCl$_2$ and (CH$_3$COO)$_2$Zn]. Thereafter, the recycling of this catalyst system was studied (Experiment E).

clave under nitrogen, and is then analyzed by vapor phase chromatography.

Recycling of the catalyst

A fresh charge of reactants (cinnamaldehyde and promoters) is introduced into the autoclave containing the catalyst which has been used. The amounts introduced are the same as those in the basic experiment. The working method for the hydrogenation of the aldehyde remains the same.

The results are as follows:

| Experiment E | Duration | DC of aldehyde | YIELDS/ aldehyde reacted | | | |
|---|---|---|---|---|---|---|
| | | | ⎡OH⎤ | ⎡O⎤ | ⎡OH⎤ | Non-volatile products* |
| Fresh catalyst | 4 hours 15 min. | 100% | 94% | — | 4% | 2% |
| Recycling | 4 hours 15 min. | 63% | 84% | — | — | 16% |

*These are condensation products between aldehydes and/or between aldehyde and alcohol.

Experiment E was repeated using the working method which has just been described, except that the catalyst which has been used is reactivated in accordance with the data of Tuley and Adams, supra, before it is re-used. To do this, 50 cm.$^3$ of ethyl alcohol are poured into the autoclave containing the catalyst, and air is passed into the catalyst suspension for 1 hour at the rate of 10 l/hour. The catalyst is then washed 3 times in succession with 50 cm.³ of ethyl alcohol, before being re-used. Two successive recyclings were carried out (Experiment F). The catalyst continues to lose its activity very rapidly, as is demonstrated by the table which follows:

| Experiment F | Duration | DC of aldehyde | ⌐⌐OH | ⌐⌐O | ⌐⌐OH | Non-volatile |
|---|---|---|---|---|---|---|
| Fresh catalyst | 4 hrs. 15 min. | 100% | 93% | 1.3% | 1.9% | 3.8% |
| 1st recycling | 4 hrs. 15 min. | 88.5% | 84% | 0.9% | 0.9% | 14% |
| 2nd recycling | 4 hrs. 15 min. | 59% | 76% | — | — | 24% |

EXAMPLE 10

This example relates to the hydrogenation of 3,7-dimethyl-octa-2,6-dienal (citral) in the form of a mixture of geranial (96%) and neral (4%), employing platinum in the form of a mass containing 4.76% by weight of noble metal deposited on charcoal (specific surface area: about 1000 m.²/g.).

(a) Pre-reduction of the platinum 21 cm.³ of isopropyl alcohol containing 30% by weight of water and 0.63 g. of platinum deposited on charcoal (equivalent to 0.029 g. of metallic platinum) are introduced into a 125 cm.³ stainless steel autoclave equipped with a knock-type agitation system and connected to a supply of hydrogen under pressure.

The pre-reduction is carried out, as indicated in Examples 1 to 9, at a temperature of 100° C. under 120 bars of hydrogen, for 16 hours.

(b) Reduction of the aldehyde

After this time, the autoclave is cooled and let down, and 7.5 g. (0.05 mol) of the mixture of geranial (96%) and neral (4%) are introduced into the autoclave. The mixture contains 0.39 g. of metallic platinum/100 g. of aldehyde to be reduced.

Thereafter, the hydrogenation of the aldehyde substrate is carried out, using the working method described for Examples 1 to 7 or 9.

After the theoretical amount of hydrogen (0.05 mol) has been absorbed, the autoclave is cooled to 20° C. and then let down, and the reaction mixture is filtered under a nitrogen atmosphere. The reactor and the catalyst on the filter (placed under nitrogen) are then washed in succession with 20 cm.³ of isopropyl alcohol containing 30% by weight of water.

The filtrate is therafter analyzed by vapor phase chromatography.

(c) Recycling of the catalyst

The catalyst contained on the filter as well as a new charge of aldehyde and of solvent are introduced into the autoclave, working under a nitrogen atmosphere. The amounts introduced are the same as those of the basic experiment. The working method for the hydrogenation of the aldehyde remains the same. Sixteen successive recyclings of the catalyst are thus carried out (without ever pre-reducing the platinum before its re-use).

For all these experiments, the hydrogenation medium proves to be a mixture of 3,7-dimethyl-octa-2,6-dienol (geraniol + nerol;

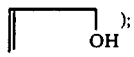

3,7-dimethyl-oct-6-enal (citronellal;

and 3,7-dimethyl-octa-6-enol (citronellol;

⌐⌐OH )

with a little unreacted starting aldehyde. The table which follows summarizes the results obtained.

| Example 10 | Duration | DC of aldehyde | ⌐⌐OH | ⌐⌐O | ⌐⌐OH |
|---|---|---|---|---|---|
| Fresh catalyst | 9 hours 30 min. | 92.2% | 99.2% | 0.8% | — |
| 1st recycling | 9 hours | 96.4% | 99.7% | 0.1% | 0.2 |
| 7th recycling | 10 hours | 97.2% | 100% | — | — |
| 16th recycling | 8 hours 50 min. | 95.5% | 97.2% | 0.4% | 2.4% |

As will be apparent to those skilled in the art, the foregoing examples can be repeated, replacing the α,β-ethylenic aldehyde starting materials with other such aldehydes as described hereinabove.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process for the preparation of α,β-ethylenic primary alcohols from the corresponding α,β-ethylenic aldehydes, which process comprises reducing an α,β-ethylenic aldehyde in the presence of hydrogen in the presence of a catalyst consisting of supported platinum which has been pre-reduced in the presence of hydrogen under pressure at a temperature of at least about 50° C.

2. A process according to claim 1, wherein the catalyst is pre-reduced at a temperature of between about 50° C. and 200° C.

3. A process according to claim 1, wherein the catalyst is pre-reduced at a temperature of between about 70° C. and 140° C.

4. A process according to claim 1, wherein the catalyst is pre-reduced at a pressure of between about 5 and 200 bars.

5. A process according to claim 1, wherein the catalyst is pre-reduced at a pressure of between about 10 and 150 bars.

6. A process according to claim 1, wherein said aldehyde is reduced at a temperature of between about 20° C. and 150° C.

7. A process according to claim 1, wherein said aldehyde is reduced at a temperature of between about 50° C. and 120° C.

8. A process according to claim 1, wherein said aldehyde is reduced at a pressure of between about 1 and 200 bars.

9. A process according to claim 1, wherein said aldehyde is reduced at a pressure of between about 5 and 100 bars.

10. A process according to claim 1, wherein said aldehyde is cinnamyl aldehyde.

11. A process according to claim 1, wherein said aldehyde is citral.

12. A process according to claim 1, wherein said catalyst is platinum dioxide.

13. A process for the preparation of α,β-ethylenic alcohols of the general formula:

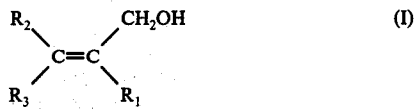

in which:
R₁ symbolizes hydrogen or:
(a) an alkyl radical having from 1 to 8 carbon atoms;
(b) a lower alkoxy radical;
(c) a cycloalkyl or cycloalkenyl radical containing from 5 to 6 carbon atoms;
(d) an aryl radical containing 1 or 2 fused benzene nuclei;
(e) an aralkyl radical containing from 1 to 2 carbon atoms in the alkyl radical and 1 or 2 fused benzene nuclei in the aryl radical.

R₂ and R₃ represent hydrogen or:
(a) alkyl radicals containing from 1 to 30 carbon atoms;
(b) lower alkoxy radicals;
(c) alkenyl radicals containing from 2 to 30 carbon atoms and from 1 to 12 conjugated or non-conjugated ethylenic double bonds;
(d) cycloalkyl or cycloalkenyl radicals containing from 5 to 8 carbon atoms;
(e) aryl radicals containing 1 or 2 fused or nonfused benzene nuclei;
(f) aralkyl radicals containing from 1 to 5 carbon atoms in the alkyl radical and 1 or 2 fused or non-fused benzene nuclei;
(g) heterocyclic radicals with 5 or 6 chain members, containing a hetero-atom selected from the group consisting of sulphur, oxygen and nitrogen;
said R₂ and R₃ can form, with R₁, an aliphatic hydrocarbon ring containing from 5 to 7 carbon atoms and 1 or 2 ethylenic double bonds, a heterocyclic ring with 5 or 6 chain members, and together, said R₂ and R₃, with the carbon atom to which they are bonded, can form an aliphatic hydrocarbon ring; which process comprises hydrogenation of an α,β-ethylenic aldehyde of the general formula:

in which:
R₁, R₂ and R₃ have the meaning given above, in the presence of a catalyst consisting of supported platinum, which is pre-reduced by prior reduction, by hydrogen, of the platinum, at a temperature of at least about 50° C.

14. A process according to claim 13, wherein in said aldehyde of the formula (II) employed, R₂ and R₃ represent the following:
R₁ and R₂ represent hydrogen, an alkyl radical having from 1 to 8 carbon atoms, or a lower alkoxy radical; and
R₃ represents an alkyl radical containing from 1 to 10 carbon atoms, an alkenyl radical containing from 2 to 30 carbon atoms and from 1 to 12 conjugated or non-conjugated ethylenic double bonds, a cycloalkyl or cycloalkenyl radical containing from 5 to 6 carbon atoms, an aryl radical containing 1 or 2 fused benzene nuclei, an aralkyl radical containing from 1 to 2 carbon atoms in the alkyl radical and 1 or 2 fused benzene nuclei, and an oxygen-containing heterocyclic radical with 5 or 6 chain members, or alternatively, R₃ forms, with R₁, a tetramethylene radical or one of the radicals:

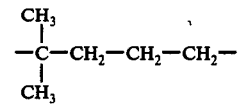

and —CH₂—CH₂—O—CH₂—, and the tetramethylene and pentamethylene radicals with R₂.

15. A process according to claim 14, characterized in that the symbols R₁, R₂ and R₃ represent the following:
R₁ represents a hydrogen atom, a methyl, ethyl, propyl, isopropyl, n-butyl, n-pentyl, n-hexyl, methoxy, ethoxy, propoxy or butoxy radical;
R₂ represents a hydrogen atom, a methyl, ethyl, methoxy or ethoxy radical;
R₃ represents one of the following radicals:
methyl, ethyl, n-propyl, n-butyl, n-pentyl, n-hexyl, n-heptyl, methoxymethyl, 2-methoxy-ethyl, [3'-methyl-cyclohex-3'-enyl]-methyl, [2',6',6'-trimethyl-cyclohex-1'-enyl]-methyl, 2-[2',6',6'-trimethyl-cyclohex-1'-enyl]-ethyl or 2-[furyl-2']-ethyl;
vinyl, prop-1-enyl, but-1-enyl, but-2-enyl, but-3-enyl, pent-3-enyl, 4-methyl-pent-3-enyl, 1,4-dimethyl-pent-3-enyl, 4,8-dimethyl-nona-3,7-dienyl, 4,8,12-trimethyl-trideca-3,7,11-trienyl, 3-[2',6',6'-trimethyl-cyclohex-1'-enyl]-1-methyl-prop-1-enyl, 5-[2',6',6'-trimethyl-cyclohex-1'-enyl]-3-methyl-penta-1,2-dienyl, 6-[2',6',6'-trimethyl-cyclohex-1'-enyl]-4-methyl-hexa-1,3,5-trienyl and 6-[furyl-2']-3-methylhex-3-enyl;
cyclohexyl and cyclohex-1-enyl;
phenyl, tolyl, benzyl and phenethyl; and furyl-2 and furyl-3.

16. A process according to claim 1, wherein the α,β-ethylenic aldehyde used is 2-methyl-but-2-enal, 3-methylbut-2-enal, hexa-2,4-dienal, octa-2,6-dienal, 3,7-dimethylocta-2,6-dienal, 3,7,11-trimethyl-dodeca-2,6,10-trienal, 9-[2',6',6'-trimethyl, cyclohex-1'-enyl]-3,7-dimethyl-nona-2,4,6,8-tetraenal, 3-phenyl-prop-2-enal, 2-n-pentyl-3-phenyl-prop-2-enal, 2-n-hexyl-3-phenyl-prop-2-enal or 3-methyl-3-phenylprop-2-enal.

17. A process according to claim 13, wherein the catalyst is pre-reduced by prior reduction, by hydrogen, at a temperature of between about 50° C. and 200° C.

18. A process according to claim 13, wherein the catalyst is pre-reduced by prior reduction, by hydrogen, at a temperature of between about 70° C. and 140° C.

19. A process according to claim 13, wherein the prereduction of the platinum is carried out at a hydrogen pressure of between about 5 and 200 bars.

20. A process according to claim 13, wherein the prereduction of the platinum is carried out at a hydrogen pressure of between about 10 and 150 bars.

21. A process according to claim 1, wherein the catalyst consists of metallic platinum deposited on charcoal, calcium carbonate, barium sulphate, aluminas, activated silicas or zeolite.

22. A process according to claim 1, wherein the catalyst consists of metallic platinum deposited on charcoal.

23. A process according to claim 13, wherein the catalyst consists of platinum dioxide.

24. A process according to claim 1, wherein the catalyst is prepared by pre-reducing, by hydrogen, in an inert liquid medium.

25. A process according to claim 24, wherein the hydrogenation of the aldehyde is carried out in an inert liquid used for the pre-reduction of the catalyst.

26. A process according to claim 24, wherein the liquid medium employed is a liquid chosen from the group consisting of saturated aliphatic hydrocarbons having from 5 to 10 carbon atoms, saturated cycloaliphatic hydrocarbons having from 5 to 12 carbon atoms, aromatic hydrocarbons containing one or two fused or non-fused benzene nuclei, alcohols, aliphatic monohydroxylic or polyhydroxylic compounds having from 1 to 10 carbon atoms, saturated cycloaliphatic alcohols having from 5 to 12 carbon atoms, their ethers, their esters derived from saturated carboxylic acids having from 1 to 6 carbon atoms, water or mixtures of water with an alcohol, ethers or esters.

27. A process according to claim 26, wherein the liquid medium employed is selected from the following:
pentane, hexane, heptane, octane, cyclopentane, cyclohexane, cycloheptane, benzene, toluene, methyl, ethyl, n-propyl, isopropyl, n-butyl, sec.-butyl, tertiary butyl and and amyl alcohols, ethylene glycol, propane-1-2-diol, butane-1,4-diol, cyclopentanol, cyclohexanol, diisopropyl ether, dioxane, dihydroxyethyl ether, the monomethyl ether of ethylene glycol, the dimethyl ether of ethylene glycol (or 1,2-dimethoxyethane), the monobutyl ether of ethylene glycol, the monomethyl ether of diethylene glycol and the dimethyl ether of diethylene glycol, ethyl acetate, amyl acetate, butyl propionate, ethylene glycol monoacetate and ethylene glycol diacetate.

28. A process according to claim 26, wherein mixtures of water with aliphatic monohydroxylic or polyhydroxylic compounds having from 1 to 4 carbon atoms are used.

29. A process according to claim 28, wherein mixtures of water and methyl alcohol, water and ethyl alcohol, water and isopropyl alcohol, water and tertiary butyl alcohol and water and ethylene glycol are used.

30. A process according to claim 1, wherein the amount of platinum, which is employed in the catalyst, is between 0.01 and 4 g. of metallic platinum per 100 g. of aldehyde to be reduced.

31. A process according to claim 1, wherein the amount of platinum, which is employed in the catalyst, is between 0.05 and 28 g. of metallic platinum per 100 g. of aldehyde to be reduced.

* * * * *